US00PP37122P2

(12) United States Plant Patent
Lim

(10) Patent No.: US PP37,122 P2
(45) Date of Patent: Dec. 2, 2025

(54) ***AGAPANTHUS* PLANT NAMED 'ALTsilverado'**

(50) Latin Name: ***Agapanthus* hybrid**
Varietal Denomination: ALTsilverado

(71) Applicant: Altman Specialty Plants llc, Vista, CA (US)

(72) Inventor: Peter Lim, Escondido, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/022,447

(22) Filed: Jan. 15, 2025

(51) Int. Cl.
*A01H 5/02* (2018.01)
*A01H 6/04* (2018.01)

(52) U.S. Cl.
USPC ..... Plt./398
CPC ..... *A01H 6/04* (2018.05)

(58) Field of Classification Search
USPC ..... Plt./398
CPC ..... A01H 5/02
See application file for complete search history.

*Primary Examiner* — Kent L Bell

(57) ABSTRACT

A new and distinct cultivar of *Agapanthus* plant named 'ALTsilverado' is disclosed, characterized by a dwarf growth habit, reaching about 35 cm high. Foliage is uniquely variegated light green, greyed-green and creamy white. Flowering stems (scapes) are thick and uniquely light green. Flowers are light blue. The new variety is an *Agapanthus*, typically produced as an ornamental plant.

2 Drawing Sheets

Figure 1:
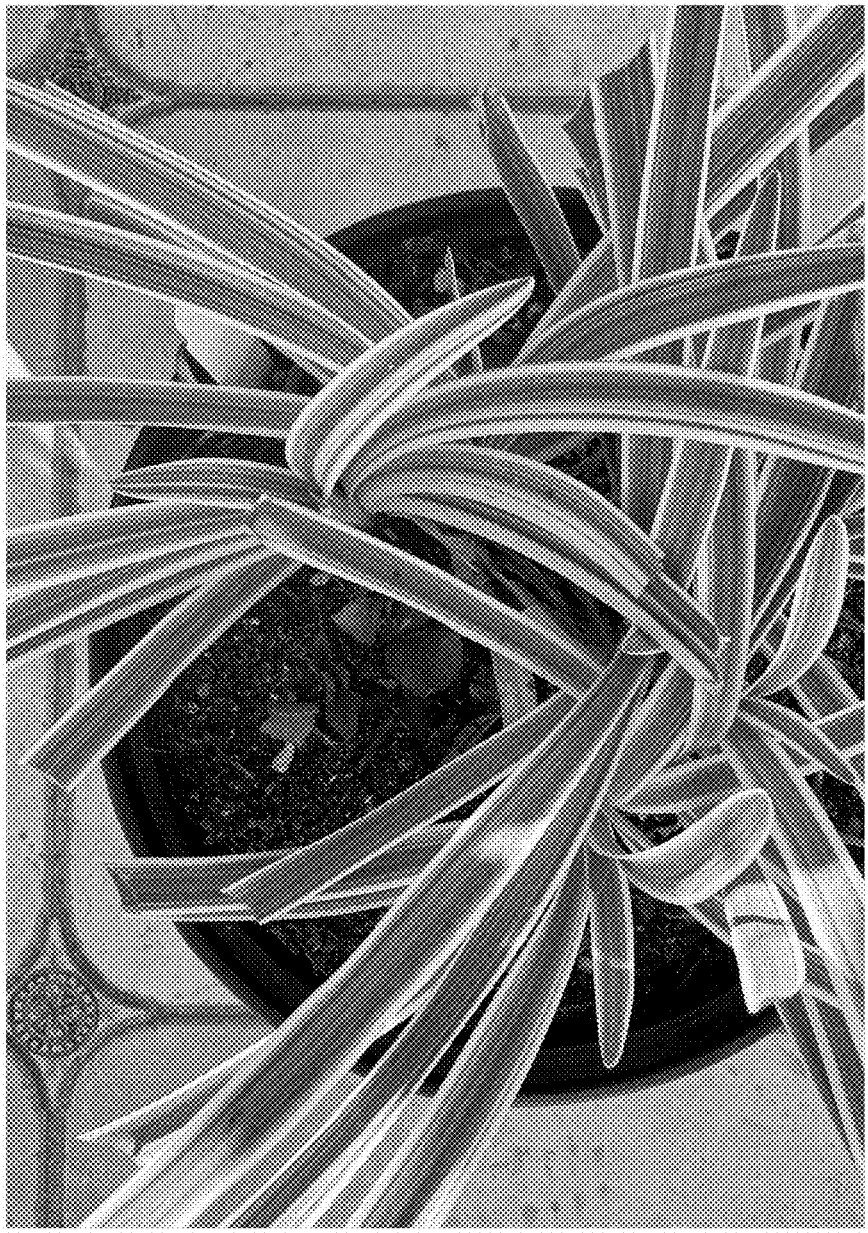

Latin name of the genus and species: *Agapanthus* hybrid.
Variety denomination: 'ALTsilverado'.

BACKGROUND OF THE INVENTION

The new *Agapanthus* cultivar is the product of a planned breeding program conducted by the inventor, Peter Lim. The cross resulting in this new variety was made in September of 2016 at a commercial nursery in Vista, California.

The seed parent is an unnamed, unpatented proprietary *Agapanthus*. The pollen parent is a different unnamed, unpatented proprietary *Agapanthus*. The new variety was identified and selected as a potentially interesting selection in June of 2019, at a commercial nursery in Vista, California.

Asexual reproduction of the new cultivar 'ALTsilverado' was first performed Jun. 10, 2019, in Vista, California, by vegetative rhizome division. Subsequent propagation has shown that the unique features of this cultivar are stable and reproduced true to type in successive generations.

SUMMARY OF THE INVENTION

The cultivar 'ALTsilverado' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTsilverado'. These characteristics in combination distinguish 'ALTsilverado' as a new and distinct *Agapanthus* cultivar:

1. Dwarf size, reaching about 35 cm.
2. Variegated light green, greyed-green and creamy white foliage.

3. Light green scapes.
4. Light blue flowers.

PARENT COMPARISON

Plants of the new cultivar 'ALTsilverado' are similar to the seed parent, in most horticultural characteristics. However, characteristics of the new cultivar differ in the following:

1. The new variety has light blue flowers; the seed parent has medium purple flowers.

Plants of the new cultivar 'ALTsilverado' are similar to the pollen parent, in most horticultural characteristics. However, the new cultivar differs in the following:

1. The new variety is shorter than the pollen parent.
2. The new variety has different variegation colors than the pollen parent.

COMMERCIAL COMPARISON

Plants of 'ALTsilverado' are similar in some horticultural characteristics to the variety *Agapanthus* 'Tinkerbell', unpatented. The new variety, however, differs in the following:

1. 'ALTsilverado' has lighter blue flowers than 'Tinkerbell'.
2. 'ALTsilverado' begins flowering earlier than 'Tinkerbell'.
3. Leaf variegation of the new cultivar is creamy white with greyed-green and light green'; variegation of 'Tinkerbell' is creamy white with darker green leaf margins.

Plants of 'ALTsilverado' are similar in some horticultural characteristics to the variety *Agapanthus* 'Gold Strike', U.S. Plant Pat. No. 20,650. The new variety, however, differs in the following:

1. 'ALTsilverado' has thicker flower stems than 'Gold Strike'.

2. 'ALTsilverado' has light blue flowers; 'Gold Strike' has dark blue flowers.
3. 'ALTsilverado' has a light green scape; 'Gold Strike' has a dark purple scape.
4. Leaf variegation of the new cultivar is creamy white with greyed-green and light green; leaf variegation of 'Gold Strike' is golden yellow with medium green.

BRIEF DESCRIPTION OF THE PHOTOGRAPHS

The accompanying photograph in FIG. 1 illustrates a close-up view of the foliage of 'ALTsilverado' during Winter in Southern California.

Figure 2:
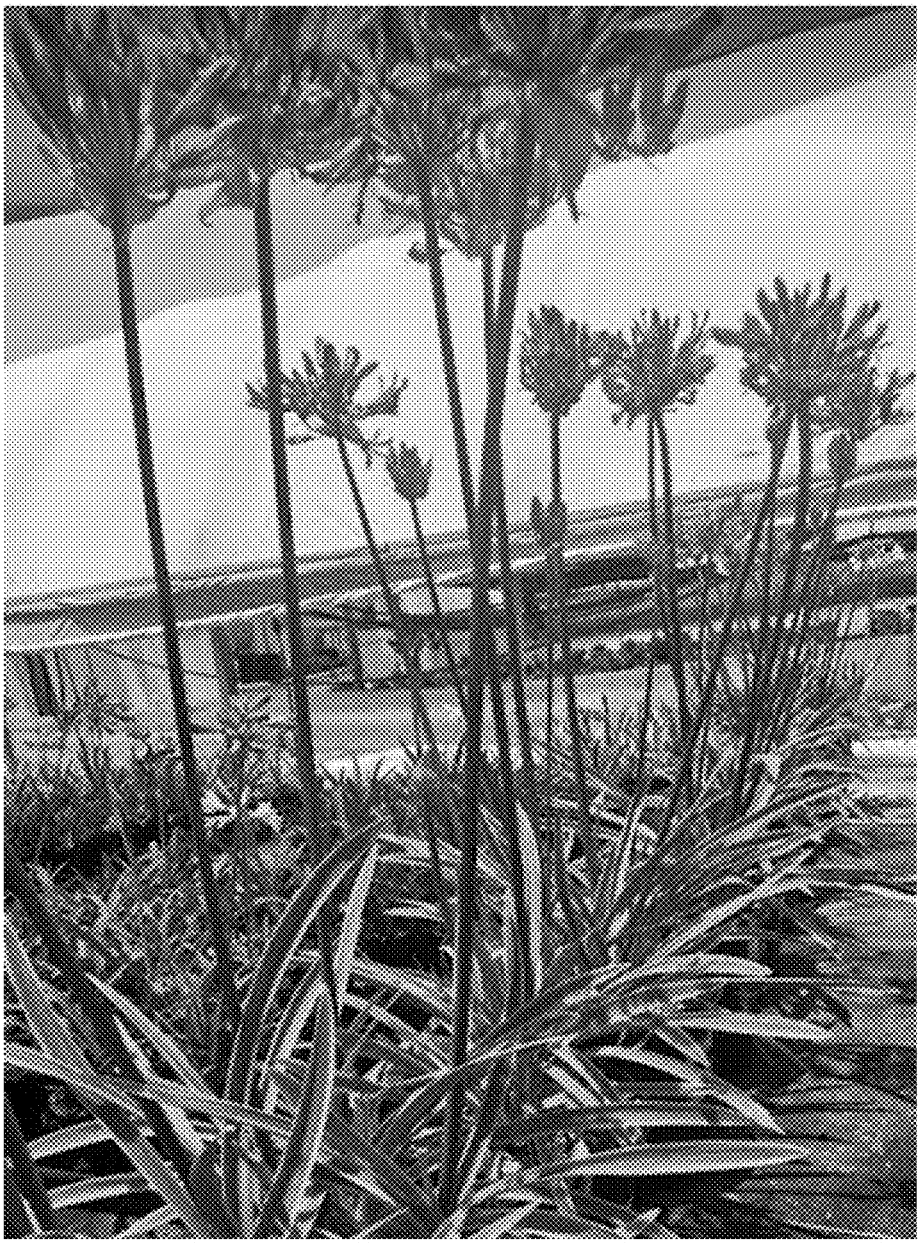

FIG. 2 illustrates in full color typical plants of 'ALTsilverado' grown in a commercial hoop-house in Vista, California. The plants are approximately one year old, grown one-gallon pots.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe an 'ALTsilverado' plant. This plant was grown outdoors in a 2-gallon pot, in Camarillo, California. Plants are approximately 1 year old. Temperatures ranged from 15° C. to 40° C. during the day, and from 10° C. to 25° C. at night. No artificial light, photoperiodic treatments were given to the plants. Measurements and numerical values represent averages of typical plant types.

Botanical classification: *Agapanthus* hybrid 'ALTsilverado'.

PROPAGATION

Propagation method: Rhizome division.

Root description: Somewhat fleshy, limited branching. Colored near Green-White 157B.

PLANT

Age of plant described: About 1-year.

Growth habit: Clump forming tender perennial with arching, pendulous foliage. Plants evergreen to about −5° C.

Height: Foliar plane 25 cm. Flowering plane 35 cm.

Plant spread: Approximately 35 cm.

Growth rate: Moderate.

FOLIAGE

Leaf:

*Arrangement*.—Basal whorls.

*Quantity*.—Average 10 to 16 per clump.

*Average length*.—15 to 25 cm.

*Average width*.—1.7 cm.

*Shape of blade*.—Linear.

*Apex*.—Acute.

*Base*.—Truncate, non-clasping.

*Margin*.—Entire.

*Aspect*.—Moderately recurved in center of clump. Outermost foliage flattens to nearly horizontal.

*Texture of top surface*.—Glabrous.

*Texture of bottom surface*.—Glabrous.

*Color*.—Young foliage upper side: Near RHS Green 138C, streaked 138B, Greyed-Green 193A and White 155A. Margin near RHS White 155A. Young foliage under side: Near RHS Green 138C, streaked 138B, Greyed-Green 193A and White 155A. Margin near RHS White 155A. Overlaid slightly Greyed-Green 196D. Mature foliage upper side: Near RHS Green 138C, streaked 138B, Greyed-Green 193A and White 155A. Margin near RHS White 155A. Mature foliage under side: Near RHS Green 138C, streaked 138B, Greyed-Green 193A and White 155A. Margin near RHS White 155A.

FLOWER

Natural flowering season: Begins flowering in May or early June in Southern California.

Length of flowering period: Approximately 8 weeks.

Inflorescence type: Terminal Umbel with approximately 25 to 30 individual flowers and 8 to 9 buds.

Individual flower type: Single.

Flower profile: Funnelform.

Lasting quality: Inflorescence shows no significant signs of aging for approximately 5 to 6 weeks.

Bud: Measured at approximately 2 to 5 days from opening.

*Shape*.—Narrow ovate.

*Length*.—Approximately 3 cm.

*Diameter*.—Approximately 10 mm.

*Color*.—Near RHS Violet-Blue 94B streaked 94A.

Umbel size:

*Diameter*.—Average 11 cm.

*Height*.—Average 7.5 cm.

Corolla:

*Arrangement*.—Apetalous, single, campanulate flowers composed of 6 basally fused tepals, shaped into a flared trumpet.

*Length*.—Approximately 3.4 cm.

*Width*.—Approximately 2.9 cm at widest point.

*Lobe length*.—Approximately 1.9 cm.

*Lobe width*.—Average 6 mm.

*Margin*.—Entire.

*Shape*.—Lanceolate.

*Apex*.—Broadly acute or obtuse.

*Texture*.—Glabrous all surfaces.

Color:

*Tepals*.—When opening, upper surface: Near RHS Violet-Blue 94B streaked 94A. When opening, lower surface: Near RHS Violet-Blue 94B streaked 94A. Fully opened, upper surface: Near RHS Violet-Blue 94C streaked 94B. Fully opened, lower surface: Near RHS Violet-Blue 94C streaked 94B.

Sepals: Not present.

Perianth tube:

*Length*.—1.7 cm.

*Width*.—6 mm.

*Color*.—Inner surface: Near RHS Violet-Blue 94D. Outer surface: Near RHS Violet-Blue 94C.

Fragrance: Faint musty scent.

REPRODUCTIVE ORGANS

Stamens:

*Protrusion*.—Weak protrusion past the floral lobe apex.

*Filament color*.—Upper section near RHS Violet-Blue 95B lower section near 94D.

Anthers:
*Quantity.*—6.
*Length.*—Approximately 3 mm.
*Color.*—Near RHS Violet-Blue 95B.
Pistil:
*Number.*—1.
*Length.*—Approximately 2.7 cm.
*Style.*—Color: Near RHS Violet-Blue 94D.
*Stigma.*—Shape: Linear. Color: Near RHS Violet-Blue 94A.
Scape:
*Length.*—Average 28 cm.
*Width.*—8 to 11 mm.
*Texture.*—Glabrous.
*Color.*—Near RHS Green 138D.
Pedicel:
*Length.*—1.5 cm.
*Width.*—2 mm.
*Texture.*—Glabrous.
*Color.*—Near RHS Green 138C.
Fragrance: None.

OTHER CHARACTERISTICS

Seeds: Not observed.
Disease/pest resistance: Neither resistance nor susceptibility to normal diseases and pests of *Agapanthus*.
Temperature tolerance: Not tested but expected to tolerate −5° C. to about 40° C.
Drought tolerance: Will tolerate considerable dryness once established.

What is claimed is:

1. A new and distinct cultivar of *Agapanthus* plant named 'ALTsilverado' as herein illustrated and described.

* * * * *